(12) United States Patent
Schadt et al.

(10) Patent No.: US 9,522,875 B2
(45) Date of Patent: Dec. 20, 2016

(54) METHOD FOR TREATING OFFGASES FROM A MELAMINE PLANT

(75) Inventors: Arne Schadt, Pasching (AT); Christoph Neumeuller, Ennsdorf (AT)

(73) Assignee: Casale SA, Lugano-Besso (CH)

( * ) Notice: Subject to any disclaimer, the term of this patent is extended or adjusted under 35 U.S.C. 154(b) by 202 days.

(21) Appl. No.: 14/005,942

(22) PCT Filed: Mar. 22, 2012

(86) PCT No.: PCT/EP2012/055071
§ 371 (c)(1),
(2), (4) Date: Sep. 18, 2013

(87) PCT Pub. No.: WO2012/126979
PCT Pub. Date: Sep. 27, 2012

(65) Prior Publication Data
US 2014/0005436 A1    Jan. 2, 2014

(30) Foreign Application Priority Data
Mar. 24, 2011   (EP) ..................... 11159553

(51) Int. Cl.
   *C07C 273/02*   (2006.01)
   *C07C 273/12*   (2006.01)
(52) U.S. Cl.
   CPC ........... *C07C 273/02* (2013.01); *C07C 273/12* (2013.01); *Y02P 20/125* (2015.11)

(58) Field of Classification Search
   CPC ............................ C07C 273/02; C07C 273/12
   See application file for complete search history.

(56) References Cited

U.S. PATENT DOCUMENTS

| 3,723,430 A | 3/1973 | Kokubo et al. |
| 6,586,629 B1 | 7/2003 | Coufal |

FOREIGN PATENT DOCUMENTS

| CN | 1329591 A | 1/2002 |
| WO | 2004011419 A1 | 2/2004 |
| WO | 2005080321 A1 | 9/2005 |
| WO | 2008052640 A1 | 5/2008 |

*Primary Examiner* — Fereydoun G Sajjadi
*Assistant Examiner* — Mark Luderer
(74) *Attorney, Agent, or Firm* — The Webb Law Firm

(57) ABSTRACT

Disclosed is a method for treating or using offgases obtained in a melamine plant comprising at least one melamine synthesis reactor and at least one washing unit in an integrated process for urea and melamine production, wherein the offgases leaving the melamine synthesis reactor are fed into the washing section and the washed offgases leaving the washing section are transferred from the washing section via at least one pipeline connecting the washing section and the at least one urea synthesis plant to the at least one urea synthesis plant. The washed offgases leaving the washing section are mixed with at least one carbamate solution immediately downstream of the washing section by feeding the carbamate solution into the pipeline connecting the washing section to the urea plant.

Figure 1:
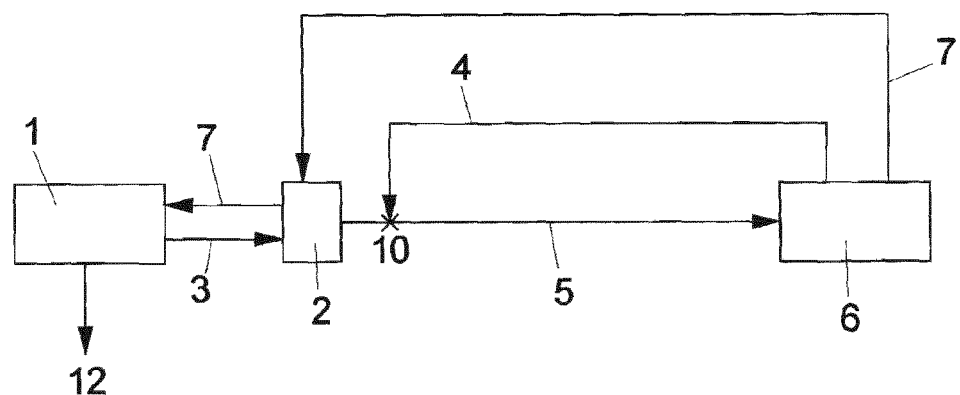

15 Claims, 3 Drawing Sheets

METHOD FOR TREATING OFFGASES FROM A MELAMINE PLANT

CROSS-REFERENCE TO RELATED APPLICATIONS

This application is the United States national phase of International Application No. PCT/EP2012/055071 filed Mar. 22, 2012, and claims priority to European Patent Application No. 11159553.4 filed on Mar. 24, 2011, the disclosures of which are hereby incorporated by reference in their entirety.

BACKGROUND OF THE INVENTION

Field of the Invention

The present invention relates to a process for treating offgases and an integrated urea melamine plant.

The present invention relates to a method for treating offgases which are obtained in a melamine synthesis reactor which is part of an integrated process for melamine and urea production.

Description of Related Art

Integrated processes for urea and melamine production have been known, wherein melamine is produced in a melamine plant, in particular in a melamine synthesis process of the low pressure type or high pressure type. Melamine synthesis uses ammonia and urea as raw material, wherein the urea is being produced in a urea production plant, to which the offgases coming from the melamine synthesis plant or reactor which substantially contain ammonia and carbon dioxide are recycled as raw materials.

In case of high pressure processes for the synthesis of melamine urea and ammonia are reacted at temperatures between 320 and 450° C. and pressures between 5 to 60 MPa whereby liquid melamine and offgases, which mainly consist of ammonia, carbon dioxide and low amounts of gaseous melamine are obtained. After separating the melamine melt from the offgases said melamine melt is being processed using different methods for obtaining pure melamine. The offgases are preferably recycled to a urea plant.

Before recycling the offgases to the melamine plant said offgases have to be treated in order to remove the gaseous melamine and further side products, since said gaseous melamine and side products can hamper the urea production.

Different methods for recycling the offgases to the urea plant comprising the step of removing gaseous melamine and its side products from the offgases before recycling the offgas to the urea section are known.

According to U.S. Pat. No. 3,723,430 the offgases leaving the high pressure melamine synthesis reactor enter an offgas washing unit, wherein the offgases are washed or scrubbed with urea melt. The urea leaving the washing section contains now the remaining melamine and side product and is fed directly to the melamine synthesis reactor. The purified or scrubbed melamine offgases are subsequently directly transferred into a low pressure urea reactor without condensation.

WO 2005/080321 A1 relates to an integrated process for urea and melamine production wherein the offgases resulting as by-products of the melamine synthesis are washed or scrubbed with urea solution or melt in a washing unit or scrubber unit and are subsequently fed to an offgas condensation section. In said condensation section the offgases coming from the melamine synthesis section and a carbamate aqueous solution are mixed together and condensed. The carbamate solution stems from the urea recovery section of the urea plant. In the condenser unit the offgases are completely condensed in the carbamate solution by indirect heat exchange with a cooling fluid, such as water, so that a concentrated carbamate aqueous solution is obtained which is subsequently fed back to the urea synthesis section.

WO 2008/052640 A1 relates also to an integrated process for urea and melamine production, wherein the urea plant is of the total recycle type and the melamine plant is a high pressure plant. The offgases of the melamine synthesis are scrubbed or washed with liquid urea in a scrubber unit and are obtained at a pressure of at least 0.2 MPa, usually with a pressure of 1 to 7 MPa. The condensation of the offgases takes place in the medium pressure section of the urea plant, wherein the condensation is carried out using an aqueous carbamate solution recycled from the urea synthesis. The medium pressure section of the urea plant has the same pressure as the offgases from the melamine plant. Therefore, the condensation takes place at the pressure of the offgases. The aqueous carbamate solution used for condensation is only mixed with the offgases from the melamine synthesis section in the condensation section.

Thus, conventional methods for treating offgases coming from a melamine synthesis reactor are washed in a washing unit or scrubber unit using liquid urea. The offgas washing allows for a purification of the offgases from gaseous melamine and side products and leave the head of the washing unit usually with a temperature between 195 to 205° and a pressure above 10 MPa. These offgases are then transferred directly, i.e. in gaseous form, or after their condensation to an aqueous carbamate solution to the high pressure part of the urea plant, wherein the offgases are used for urea synthesis.

Although the offgases leaving the offgas washing unit comprise practically only ammonia and carbon dioxide and are therefore dry, undesired corrosion phenomena are recognized in the offgas pipeline connecting the washing unit of the melamine plant to the urea plant. These undesired corrosion phenomena may be due to small traces of water, which favour the condensation of the offgases to carbamate. Another reason for the corrosion phenomena may be that the condensation of the offgases is caused by bad insulation which in turn causes a decrease of the temperature of the offgases and subsequently in combination with traces of water, a condensation of the offgases.

It is known that carbamate is a high corrosive liquid (Nitrogen, September/October 1996, Nr. 223, pages 39 to 48). In order to avoid or reduce the undesired corrosion caused by the carbamate liquid it has been suggested to flush the synthesis equipment, in particular, the pipelines being in contact with the carbamate solution with passivating air. Passivating air may be additionally enriched with oxygen. The passivating air promotes the formation of stable oxide layers on the inside surfaces of the equipment and prevents therefore corrosion. The passivating air is for instance introduced into the upper area of the urea scrubber and flushes therefore also the offgas pipelines.

A further reason for the corrosion detected in offgas pipelines can be seen in that solid particles carried over are deposited locally in the offgas pipeline, for instance at locations where the surface is uneven due to welding seams. These deposits can prevent the contact of the metal surface with the passivating air; thereby corrosion can occur at these locations.

The offgas pipeline for transferring the offgases from the melamine plant to the urea plant is the central connecting pipeline between both plants and may have a length of up to several hundred meters. For instance, it is not unusual that the connecting pipeline in particular in older plants can have a length between 200 to 300 m, whereas in newer plants the length of the pipeline can be reduced to about 10 or 20 m. However, due to the strong corrosion problems encountered in these offgas pipelines it is necessary to shut down the complete plant complex in order to carry out the necessary repair. This is however cost intensive and therefore not desirable.

It is also known that the corrosion phenomenon increases with increasing temperature. Therefore, a possible approach for reducing the corrosion in the offgas pipeline after or downstream of the urea scrubber may be to decrease the temperature of the offgases coming from the scrubber. This could be for instance done by operating the offgas scrubber on a lower temperature level. The disadvantage of this approach is, however, that the offgas heat cannot be used as usual for the pre-heating of the urea melt entering the melamine reactor.

Another approach could be to feed water into the offgas pipeline. This, however, would be contra productive for the urea synthesis, since additional water negatively influences the synthesis rate of urea and would lead to a higher consumption of operating material like steam. Furthermore, it would be necessary to remove the water from the offgases before entering the urea plant.

SUMMARY OF THE INVENTION

It is therefore an objective of the present invention to provide a method and a device which allows for reducing the corrosion in an offgas pipeline connecting a melamine plant to a urea plant without encountering the problems described in the prior art.

The method according to and exemplary embodiment of the invention is related to treating offgases obtained in a melamine plant comprising at least one melamine synthesis reactor and at least one washing unit, in particular a high pressure melamine synthesis plant, in an integrated process for urea and melamine production. The offgases leaving the melamine synthesis reactor as part of the high pressure melamine plant are fed into said washing section, which is also known as a urea scrubber.

The washed offgases leaving the washing section or scrubber are transferred from said washing section via at least one pipeline to at least one urea synthesis plant. This means that the pipeline connects the said washing section and therefore the melamine plant to the at least one urea synthesis plant.

The present method the washed offgases leaving the washing section or scrubber are mixed with at least one carbamate solution downstream of the washing section, i.e. immediately after leaving the washing section. The mixing is carried out by feeding the carbamate solution into the pipeline connecting said washing section to said urea plant.

The method according to the invention is characterized in that the volume ratio of offgases to carbamate solution fed to the pipeline is chosen such that a two phase mixture of offgases and carbamate solution is obtained within the pipeline.

Thus, when mixing the offgases from the washing unit with the carbamate solution fed into the pipeline a two phase mixture or product of gaseous offgases and liquid carbamate (gas/liquid) is obtained within the pipeline connecting the melamine and urea plant. The feeding of the aqueous carbamate solution into the pipeline can also be seen as an additional step of the washing process taking place in the washing unit or scrubber.

The ratio of offgases and carbamate solution is thus chosen such that at least an amount of carbamate solution is fed which enables a partial offgas condensation beyond the saturation point of the offgases. Thus, the volume ratio of offgases to carbamate solution fed to the pipeline is between 2:1 and 10:1, preferably 2:1 and 8:1, most preferably between 2.3:1 and 5:1. The feeding of aqueous carbamate solution into the offgas pipeline reduces surprisingly the corrosion effects in the pipeline although highly corrosive carbamate is present. Thereby, the corrosive carbamate present in the pipeline consists of the carbamate solution fed into the pipeline as well as additional carbamate formed by condensation of the offgases.

This effect of decreasing or reducing the corrosion was not predictable based on the prior art. Although the feeding of the carbamate solution reduces the temperature of the offgases—what would decrease corrosion as such—the corrosive properties of an aqueous carbamate solution would usually counteract this effect and would increase the corrosion. Furthermore, when mixing the offgases and the carbamate solution at least a partial condensation of the melamine offgases occur and thus further concentrated carbamate solution is formed even enforcing the corrosive effect.

In contrast to the expected phenomena as just described the method according to the invention strongly reduces the corrosion in the pipeline. It is assumed that a liquid film is formed in the lower parts of the horizontal offgas pipeline due to at least a partial condensation of the offgases. Said film is overlaid by the offgas stream and effects a flushing. The flushing in turn prevents the deposition of solid particles, and also rust particles, otherwise promoting the corrosion.

The term "immediately" in the context of the present invention means that the carbamate solution is fed into the pipeline using an appropriate inlet close or near to the outlet of the washing unit or scrubber, i.e downstream of the washing unit. This means that the distance between washing or scrubber outlet, in particular an expansion valve or pressure control valve of the washing section or scrubber, and at least one location such as an inlet for the carbamate solution arranged on the pipeline is preferably small.

The distance between outlet of the washing unit and the inlet for feeding carbamate solution depends on the overall length of the connecting pipeline.

In an embodiment the present process the inlet for feeding the carbamate solution to the connecting pipeline is arranged at a position or location within a distance from the washing section being ⅓, preferably being ¼ of the overall length of the connecting pipeline.

Thus, in cases where the overall length of the connecting pipeline is several hundred meters such as 200 to 300 m, the distance of the inlet from the outlet of the washing section is not larger than 100 m, preferably 50 m, more preferably 20 m, most preferably 10 m. In cases where the overall length of the connecting pipeline is 10 to 20 m the distance of the inlet to the outlet of the washing section is 6 m, preferably 5 m, more preferably 3 m, most preferably 1 m.

In a preferred embodiment of the invention the at least one carbamate solution is fed into the pipeline connecting the washing section to the urea plant at at least one downstream location such as an inlet having a distance of 5 m from the washing section or scrubber. Thus, according to this embodiment, the distance between the outlet of the washing section or scrubber such as a suitable expansion valve or pressure control valve and at least one inlet for feeding the carbamate solution such as a suitable nozzle is preferably 5 m. However, it is in general also conceivable to reduce the distance between scrubber outlet and carbamate inlet even further. The distance between scrubber outlet and carbamate inlet could also be between 0.5 and below 5 m, preferably 1 to 3 m.

In another preferred embodiment of the present method the washing section comprises a vertical washing apparatus with an expansion valve or pressure valve, which can be arranged in a predetermined distance such as 1 to 5 m, preferably 2 to 5 m in vertical direction from the washing apparatus.

The connecting pipeline continues further vertically from said expansion valve or pressure valve of the vertical washing section for a predetermined distance to a point where the connecting pipeline is bent by a predetermined angle, preferably by at least 90°, most preferably in an angle between 90 and 110°.

The distance or length of the connecting pipeline between expansion valve or pressure valve and the bending point of the pipeline is usually chosen in dependency of the space locally available, but can be for instance between 1 to 5 m, preferably 2 to 5 m.

After the bending point or curvature point the connecting pipeline continues subsequently horizontal or with a predetermined decline towards the urea plant, wherein the decline is determined by the bending angle mentioned above, for connecting the washing section and the urea plant. Subsequently, the at least one carbamate solution is then fed into the connection pipeline at an inlet having a distance of at least 5 m, preferably 3 m, most preferably 1 m from said bending point of the connecting pipeline.

In another exemplary embodiment the at least one carbamate solution comprises between 10 and 50 wt % $CO_2$ and between 10 and 50 wt % $NH_3$. The temperature of the fed carbamate solution is preferably between 60 to 90° C. and has a pressure which is equal to the pressure in the high pressure part of the melamine plant, that is between 3 and 15 MPa, preferably between 8 and 12 MPa. In general the pressure of the carbamate solution to be fed into the pipeline should be higher than the pressure of the offgases fed into the pipeline, i.e. the pressure in the high pressure part of the melamine plant, in order to fed or inject the carbamate solution into the pipeline.

The temperature of the offgases leaving the washing section at the head of the urea scrubber is between 190 and 250° C., preferably between 195 and 230° C., most preferably between 195 and 205° C. The offgases usually have a pressure above 3 MPa, preferably above 8 MPa.

After mixing the carbamate solution and the offgases leaving the washing section the temperature of the mixture in the pipeline is adapted to a value between 140 and 200° C., preferably between 150 and 190° C.

In a particular preferred embodiment the at least one carbamate solution stems from said urea plant, in particular from the low pressure part of said urea plant. It is preferred that the carbamate solution originating from a urea plant as the product of non-converted $NH_3$ and $CO_2$ is recycled in a process of the total recycle type wherein the recycling comprises a stripping process. In said stripping process carbamate is decomposed in several steps with decreasing pressure in a medium pressure and/or low pressure part of the urea plant into $NH_3$, $CO_2$ and water which is in turn recycled to the urea synthesis reactor.

Such a combination of urea synthesis and recycling process is for instance known as the Snamprogetti Ammonia- and Self-stripping process (Ullmann's Encyclopedia of Industrial Chemistry, 6th edition, 2005, Chapter Urea, pages 1 to 36). This process comprises the steps of urea synthesis by feeding $CO_2$, $NH_3$ and recycled carbamate into a urea synthesis reactor, subsequently transferring the synthesis mixture to a medium pressure recirculation and a low pressure recirculation wherein the carbamate solution is separated from the urea product using stripping processes and the carbamate solution is recycled to the urea synthesis reactor. The obtained urea is then further treated in a finishing process.

As previously mentioned it is preferred in the context of the present invention to feed a carbamate solution originating from such a urea recycling process into the pipeline connecting the urea scrubber of the melamine plant and the urea plant. Thereby the carbamate solution may stem from a medium pressure section, the low pressure section and/or any other section of a urea stripping process. It is however preferred to use carbamate solution from the low pressure section of the urea stripping process. It is also possible to add carbamate solution from any other suitable source.

In an exemplary embodiment the carbamate solution is fed into the said pipeline connecting said washing section to said urea plant at more than one location such as an inlet along the pipeline, preferably up to four locations or inlets. This means that the feeding of the carbamate solution is not restricted to one location immediately downstream of the washing unit. However, it is within the meaning of the present invention that carbamate solution has to be fed at least at the location closest to the washing unit.

In an exemplary embodiment of the invention at least 20% of the total amount of carbamate solution is fed into the said pipeline connecting said washing section to the urea plant at the first inlet or location on the pipeline immediately after leaving said washing section, i.e. immediately downstream of the washing section or scrubber such as within 5 m downstream of the washing section or scrubber. In a particular preferred embodiment 100% of the carbamate solution is introduced into the pipeline at the first location or carbamate inlet.

The carbamate solution can be fed into the pipeline connecting the washing section to the urea plant using at least one nozzle or injector as inlet for the carbamate solution. The nozzle or injector can be arranged at the pipeline with an angle between 0 and 90 degree in respect to the direction of flow in the pipeline. It is also possible to install mixing devices at the feeding location which allow for mixing the carbamate solution coming from the urea plant with fresh $NH_3$ or $CO_2$ if necessary.

Due to the lower temperature of the carbamate solution coming preferably from the urea stripping section having a temperature between 60 and 90° C. at least a partial condensation within the pipeline occurs when feeding the carbamate solution into the offgas pipeline. The aqueous carbamate solution supports the condensation of the offgas and is subsequently recycled to the urea reactor together with the condensed offgas. An advantage of this approach is that the recycling can be carried out without adding water into the urea synthesis reactor.

In a further embodiment the mixture of offgases and carbamate solution obtained in the pipeline is fed to at least one condenser unit before entering the urea synthesis reactor as part of the urea plant. By doing so a complete or partial condensation of the offgases present in the mixture of offgases and carbamate solution takes place in said condenser unit which is preferably located immediately upstream such as 1 to 5 m of the urea synthesis reactor. The condenser unit as just described can also be seen as part of the urea synthesis plant.

In a particular preferred embodiment the mixture of offgases and carbamate solution obtained in the at least one pipeline is fed immediately after mixing the offgases and the carbamate solution into at least one condenser unit, wherein a complete or partial condensation of offgases and carbamate solution takes place.

In this case the condenser unit is preferably located immediately downstream of the washing unit with a distance which depends on the overall length of the connecting pipeline. Thus, in cases where the overall length of the connecting pipeline is several hundred meters such as 200 to 300 m, the distance of the condenser is not larger than 100 m, preferably 50 m, more preferably 20 m from the outlet of the washing unit or section. In cases where the overall length of the connecting pipeline is 10 to 20 m the distance of the condenser to the outlet of the washing section is 8 m, preferably 5 m, more preferably 3 m. In this case not only the feeding of a carbamate solution into the offgas pipeline may take place, but also heat dissipation occurs in the condenser so that a complete offgas condensation is achieved almost immediately downstream of the washing unit of the melamine plant. This allows for a reduction of the offgas pipeline between the melamine plant and the urea plant and therefore for reducing costs even further.

In another preferred embodiment the mixture of offgases and carbamate solution obtained in said offgas pipeline is fed to at least two condenser units arranged between the washing unit of the melamin plant and the urea plant, in particular the urea synthesis reactor, wherein in a first condenser unit a partial condensation of offgases and carbamate solution takes place and in the second condenser unit a complete condensation of offgases and carbamate solution takes place.

The process according to the invention is carried out in an integrated urea-melamine plant comprising at least one melamine plant comprising at least one melamine synthesis reactor and at least one washing section for the offgases leaving the melamine synthesis reactor; and at least one pipeline connecting the at least one melamine plant, in particular the at least one washing section, to at least one urea plant comprising at least one urea synthesis reactor. The integrated urea-melamine plant comprises further at least one inlet, in particular for feeding carbamate solution into said pipeline for obtaining a two phase mixture comprising said offgases and said carbamate solution, wherein said inlet is located immediately downstream, of the washing section at said pipeline.

Again, the distance between outlet of the washing unit and the inlet for feeding carbamate solution depends on the overall length of the connecting pipeline and is preferably ⅓, most preferably ¼ of the overall length of the connecting pipeline. Thus, in cases where the overall length of the connecting pipeline is several hundred meters such as 200 to 300 m, the distance of the inlet from the outlet of the washing section is not larger than 100 m, preferably 50 m, more preferably 20 m, most preferably 10 m. In cases where the overall length of the connecting pipeline is 10 to 20 m the distance of the inlet from the outlet of the washing section is 6 m, preferably 5 m, more preferably 3 m, most preferably 1 m.

The integrated urea-melamine plant comprises in a preferred embodiment at least one condenser unit for a partial or complete condensation of the mixture comprising said offgases and said carbamate solution, wherein said condenser unit is located immediately downstream of said washing section and said inlet. Thus, a condenser unit is located downstream of the inlet for feeding the carbamate solution into the pipeline. The distance of this condenser unit from the scrubber outlet is preferably as described previously.

In a most preferred embodiment the integrated urea-melamine plant comprises at least one inlet at the pipeline between melamine and urea plant for feeding carbamate solution located in a distance of 5 m downstream of the outlet of the melamine washing section and at least one condenser unit arranged in a distance of 20 m downstream of the outlet of the washing section. Thus, the preferred distance between carbamate inlet and condenser unit is 15 m.

In another embodiment the integrated urea-melamine plant comprises at least one condenser unit for a partial or complete condensation of the mixture comprising said offgases and said carbamate solution located immediately upstream of said urea synthesis reactor.

It is also possible that the integrated urea-melamine plant comprises at least one condenser unit for a partial condensation of the mixture comprising said offgases and said carbamate solution located immediately downstream of said washing section and at least one condenser unit for a complete condensation of the mixture comprising said offgases and said carbamate solution located immediately upstream of said urea synthesis reactor. The two condenser units may however also be arranged anywhere alongside the pipeline connecting washing section of the melamine plant and the urea synthesis reactor of the urea plant.

The integrated urea-melamine plant may also comprise more than one inlet, in particular up to four inlets for feeding carbamate solution into said pipeline for obtaining a mixture comprising said offgases and said carbamate solution.

Figure 2:
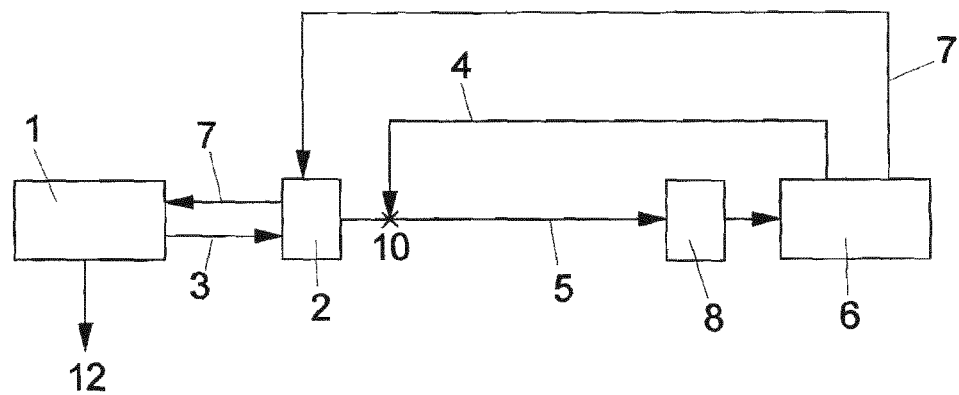
Figure 3:
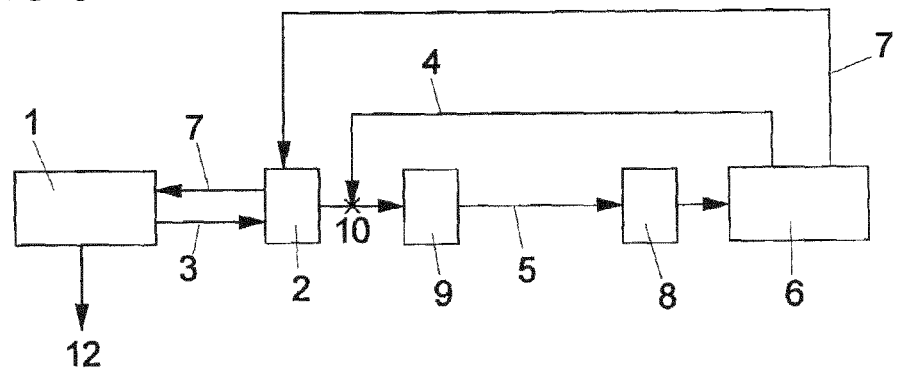
Figure 4:
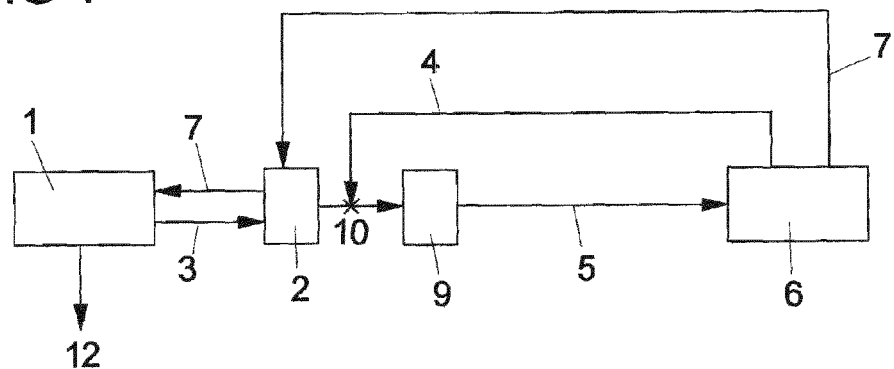
Figure 5:
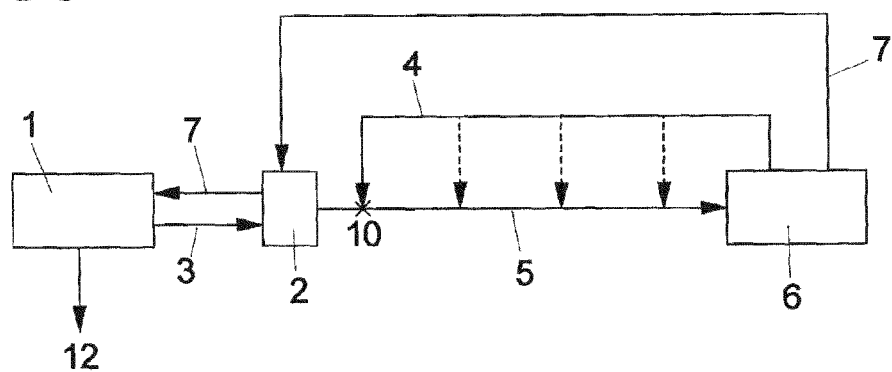
Figure 6:
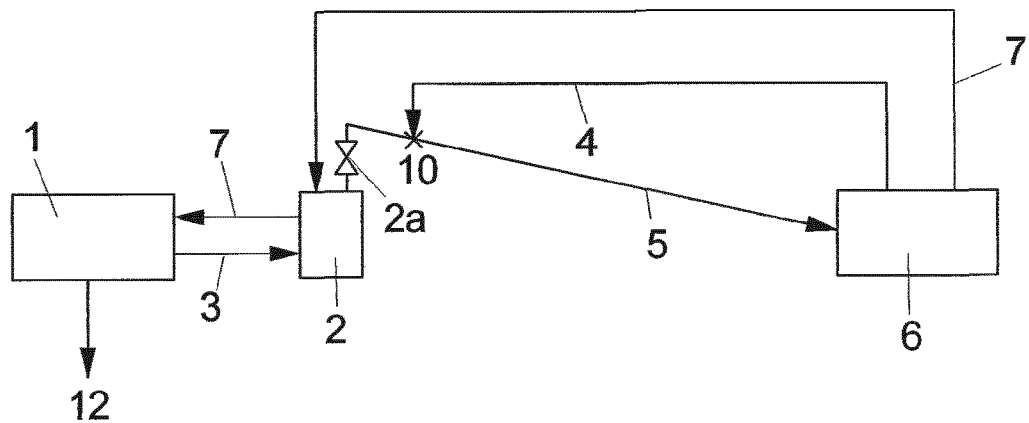

The present invention is further explained in more detail based on the following examples in conjunction with the Figures. It shows:

FIG. 1 a scheme of an integrated urea-melamine-plant according to a first embodiment of the invention;

FIG. 2 a scheme of an integrated urea-melamine-plant according to a second embodiment of the invention;

FIG. 3 a scheme of an integrated urea-melamine-plant according to a third embodiment of the invention;

FIG. 4 a scheme of an integrated urea-melamine-plant according to a fourth embodiment of the invention;

FIG. 5 a scheme of an integrated urea-melamine-plant according to a fifth embodiment of the invention, and FIG. 6 a scheme of an integrated urea-melamine plant according to a sixth embodiment of the invention.

FIG. 1 shows a scheme of an integrated urea-melamine-plant according to a first embodiment of the invention, wherein the melamine plant comprises a melamine synthesis reactor 1 and a urea scrubber 2. In the melamine synthesis reactor 1 urea 7 coming preferably from the urea plant 6 comprising a urea synthesis reactor and further work-up sages is reacted in the presence of $NH_3$ to melamine. The melamine melt 12 contains melamine as the main product as well as the offgases 3 $NH_3$ and $CO_2$ and side products as for instance the melamine condensation products melem or melam and oxidation products of melamine like as ammeline and ammelide.

The offgases 3 are separated from the melamine melt 12. The latter one leaves the melamine synthesis reactor 1 and is subjected to several purification steps which may include a quenching process of the melamine melt with ammonia or an alkali containing solution and further work up of the solidified melamine. These processes are well known to a person skilled in the art.

The offgases 3 comprise mainly $NH_3$, $CO_2$, but also gaseous melamine and eventually melamine side products. In order to recycle $NH_3$ and $CO_2$ for urea production it is desired to remove the gaseous melamine and the side products from the offgas stream. Therefore the offgases 3 coming from the melamine reactor are transferred to a washing unit or urea scrubber 2. Here the offgas stream 3 is washed or scrubbed with urea 7 coming from the urea plant. The urea 7 scrubs or washes the offgas by removing the gaseous melamine and side products from the offgas stream. Simultaneously, the urea 7 is heated by the offgases 3 which usually have a temperature between 195 and 205° C. The urea 7 leaving the scrubber 2 is then fed to the melamine synthesis reactor 1.

The offgases 3 free of gaseous melamine and its side products leave the urea scrubber 2 at the head of the scrubber 2 through an appropriate outlet into the pipeline 5 connecting the urea scrubber 2 and the urea plant 6. The urea plant 6 comprises an urea synthesis reactor and at least one recirculation stage (not shown). Immediately downstream of the outlet of the scrubber 2 an inlet 10 for feeding carbamate solution 4 into the pipeline 5 is provided. The carbamate solution 4 is a side product of the urea synthesis and is diverted from one of the carbamate recirculation stages, like for instance the low pressure recirculation section (not shown) as part of the urea plant 6.

The inlet 10 is arranged in form of a nozzle downstream of the scrubber 2 with a distance from the latter one of less than 10 m, such as 5 m. The inlet or nozzle 10 is arranged with an angle of 45° C. in respect to the direction of flow and to the pipeline 5. This allows for a rapid mixing of the carbamate solution 4 with the offgas stream 3.

The carbamate solution 4 is fed into the pipeline 5 via inlet 10 having a temperature between 60 to 90° C. Due to the lower temperature of the carbamate solution 4 the offgases 3 are cooled and a partial condensation of the offgases 3 takes place at the feeding location within the pipeline 5.

The mixture of offgases 3 and liquid carbamate solution 4 is a two phase system, i.e. a gaseous-liquid system, which is subsequently transferred through the pipeline 5 directly into the urea synthesis reactor in the urea plant 6 where the mixture is mixed with fresh $NH_3$ and $CO_2$ and recycled carbamate solution.

As described further below by the means of examples the feeding of aqueous carbamate solution 4 into the offgas pipeline 5 and thus mixing the offgases 3 with the carbamate solution 4 reduces surprisingly the corrosion effects in the pipeline although highly corrosive carbamate is used.

Thus, the integrated urea-melamine plant as exemplarily described in FIG. 1 as well as in the following FIGS. 2 to 5 allows surprisingly for an easy and unexpected way of recycling the offgases 3 from a melamine plant into an urea plant without the need to shut down the plant for removing the corroded parts of the pipeline and thus for a more cost efficient melamine production.

FIG. 2 relates to a second embodiment of the invention and the integrated urea-melamine plant schematically shown in FIG. 2 and comprises all features of the plant of FIG. 1. Additionally, a condenser 8 is integrated into the melamine offgas 3 recycling system. The condenser 8 is arranged immediately upstream of the urea plant 6.

The condenser 8 is operated at a pressure corresponding to the pressure in the high pressure part of the melamine plant and is thus lower than the pressure in the urea plant 6. The condensed liquid is usually transported from the condenser 8 to the urea plant 6 by the means of a pump. The temperature in the condenser 8 is usually between 150 and 180° C. and thus slightly lower than in the urea plant 6 with a temperature between 190 and 200° C.

Thus, the two-phase mixture of offgases 3 and carbamate solution 4 are completely condensed in said condenser 8 and a highly concentrated carbamate solution is obtained in the condenser which is subsequently fed to the urea plant 6. It is also possible to feed fresh $NH_3$ or $CO_2$ as well as carbamate solution coming from other sources like from the medium-pressure or lower pressure urea treatment sections into the condenser 8.

FIG. 3 relates to a third embodiment of the invention and the integrated urea-melamine plant schematically shown in FIGS. 1 and 2. Additionally, a further condenser 9 is integrated into the offgas pipeline 5 between the melamine plant and urea plant.

The condenser 9 is located immediately downstream of the urea scrubber 2 and the nozzle 10 for the carbamate solution. The condenser 9 is in particular located with a distance of 20 m from the urea scrubber 2 and 15 m from the nozzle 10.

Thus, the two phase system of offgas 3 and carbamate solution 4 obtained at the inlet 10 may be partially condensed in condenser 9 providing a highly concentrated carbamate solution. The partially condensed carbamate solution is subsequently transported through pipeline 5 to the condenser 8 where it is further condensed and optionally mixed with carbamate solution from the stripping or recycling part of the urea plant or with fresh $NH_3$ and $CO_2$.

FIG. 4 relates to a fourth embodiment of the invention. The integrated urea-melamine plant of FIG. 4 comprises all features of the plant of FIG. 1. In addition to the plant of FIG. 1 a condenser 9 is arranged immediately downstream such as 20 m of the urea scrubber 2 and 15 m of the inlet 10 at the pipeline 5.

In case of the plant of FIG. 4 not only the feeding of a carbamate solution 4 into the offgas pipeline 5 takes place immediately downstream of the urea scrubber 2, but also heat dissipation occurs in the condenser 9 so that a complete offgas condensation is achieved immediately downstream of the urea scrubber 2 of the melamine plant. This allows for a reduction of the length of the offgas pipeline 5 between the melamine plant and the urea plant and therefore for reducing costs even further.

FIG. 5 relates to a fifth embodiment of the invention and comprises all features of the plant of FIG. 1. In addition to the inlet 10 for the carbamate solution 4 several further inlets, for instance 3 inlets for feeding the carbamate solution at different locations alongside of pipeline 5 may be provided. Thus, a gradual mixing of the offgases 3 from the urea scrubber 2 with the carbamate solution 4 occurs. The gradual mixing allows for a gradual temperature decrease of the offgases 3 and thus a gradual condensation. In this case at least 20% of the total amount of carbamate solution 4 is fed into the first inlet 10 located immediately downstream of the urea scrubber 2.

FIG. 6 relates to a sixth embodiment of the invention which corresponds basically to the embodiment described in FIG. 1 but with the difference that the employed washing section (2) comprises a vertical washing apparatus with an expansion valve or pressure valve (2a), which is arranged within 5 m from the washing apparatus.

Thus, the connecting pipeline (5) extends vertical from the washing section (2) and continues further vertically from said expansion valve or pressure valve (2a) of the vertical washing section for at least 1 m. At this distance the connecting pipeline (5) is bent by an angle of 100° in direction towards the urea plant (6).

After the bending point or curvature point (13) the connecting pipeline (5) continues subsequently with decline towards the urea plant (6), wherein the decline is determined by the bending angle of 100°, for connecting the washing section and the urea plant. Subsequently, the at least one carbamate solution (4) is then fed into the connection pipeline (5) at an inlet (10) having a distance of 5 m from said bending point (13) of the connecting pipeline (5).

A person skilled in the art will of course understand when reading the present invention that any combination of the embodiments shown in the accompanied Figures and described above is possible and is therefore covered by the present disclosure.

Example 1 (Comparative)

23 t/h of Offgas containing $NH_3$ and $CO_2$ originating from a high pressure melamine reactor operated at 375° C. and 10.5 MPa is directed to a urea scrubber. In the urea scrubber the offgas is contacted with cool urea melt in order to remove the traces of melamine contained in the offgas. The so purified and cooled offgas leaves the urea scrubber with 10.5 MPa and 205° C. into the offgas pipeline connecting the melamine plant and urea plant in the direction of the urea synthesis plant.

After only a short operation period of several weeks severe leakage in the offgas pipeline was observed which was due to corrosion phenomena. The whole plant had to be shut down for several days in order to replace the corroded parts of the offgas pipeline Example 2

23 t/h of Offgas containing $NH_3$ and $CO_2$ originating from a high pressure melamine reactor operated at 375° C. and 10.5 MPa is directed to a urea scrubber. In the urea scrubber the offgas is contacted with cool urea melt in order to remove the traces of melamine contained in the offgas. The so purified and cooled offgas leaves the urea scrubber with 10.5 MPa and 205° C.

In a distance of 5 m from the urea scrubber pressure regulation valve 10 t/h of carbamate solution with a temperature of 70° C. were added via a nozzle to the offgas pipeline. The temperature of the generated two-phase mixture was approx. 165° C. After subsequent total condensation of the melamine offgas in a condenser unit the obtained carbamate solution was recycled to the urea plant.

After several years of operation no corrosion was observed in the offgas pipeline.

LIST OF REFERENCE SIGNS 1 melamine synthesis reactor
2 urea scrubber
2a expansion valve or pressure valve
3 offgas from the melamine synthesis
4 carbamate solution
5 pipeline connecting melamine plant and urea plant
6 urea plant
7 urea
8 one condenser
9 another condenser
10 inlet for carbamate solution 4
11 further inlets for carbamate solution 4
12 melamine melt
13 bending point

The invention claimed is:

1. A method for using offgases obtained in a melamine plant comprising at least one melamine synthesis reactor and at least one washing section in an integrated process for urea and melamine production, wherein the offgases leaving the melamine synthesis reactor are fed into the washing section and the washed offgases leaving the washing section are transferred from the washing section via at least one pipeline, which connects the washing section to at least one urea plant, wherein the washed offgases leaving the washing section are mixed with at least one carbamate solution downstream of the washing section by feeding the carbamate solution into the pipeline connecting the washing section to the urea plant,
wherein the volume ratio of offgases to carbamate solution fed to the pipeline and is between 2:1 and 10:1 such that a two phase mixture of offgases and carbamate solution is obtained within the pipeline.

2. The method according to claim 1, wherein the volume ratio of offgases to carbamate solution fed to the pipeline is between 2:1 and 8:1.

3. The method according to claim 1, wherein the at least one carbamate solution is fed into the pipeline connecting the washing section to the urea plant at at least one inlet having a distance of ⅓ of the overall length of the connecting pipeline.

4. The method according to claim 1, wherein the pipeline continues at first vertically from said expansion valve or pressure valve of the vertical washing section for a predetermined distance to a point where the pipeline is bent by a predetermined angle and continues subsequently horizontal or with a predetermined decline towards the urea plant for connecting the washing section and the urea plant, and wherein the at least one carbamate solution is fed into the pipeline within a distance of at least 5 m after said bending point of the pipeline.

5. The method according to claim 1, wherein the at least one carbamate solution stems from the urea plant.

6. The method according to claim 1, wherein the carbamate solution is fed into the pipeline connecting the washing section to the urea plant at more than one location along the pipeline.

7. The method according to claim 1, wherein at least 20% of the total amount of carbamate solution is fed into the pipeline connecting the washing section to the urea plant after leaving the washing section.

8. The method according to claim 1, wherein the mixture of offgases and carbamate solution obtained in the pipeline is fed to at least one condenser unit before entering the urea plant, and wherein in the at least one condenser unit a complete or partial condensation of the offgases takes place.

9. The method according to claim 1, wherein the mixture of offgases and carbamate solution obtained in the at least one pipeline is fed after mixing the offgases and the carbamate solution into at least one condenser unit, and wherein a complete or partial condensation of offgases takes place.

10. The method according to claim 1, wherein the mixture of offgases and carbamate solution obtained in the pipeline is fed to at least two condenser units, and wherein in a first condenser unit a partial condensation of offgases takes place and in the second condenser unit a complete condensation of offgases takes place.

11. The method according to claim 1, wherein the volume ratio of offgases to carbamate solution fed to the pipeline is between 2.3:1 and 5:1.

12. The method according to claim 1, wherein the at least one carbamate solution is fed into the pipeline connecting the washing section to the urea plant at at least one inlet having a distance of ¼ of the overall length of the connecting pipeline.

13. The method according to claim 1, wherein the pipeline continues at first vertically from said expansion valve or pressure valve of the vertical washing section for a predetermined distance to a point where the pipeline is bent by a predetermined angle and continues subsequently horizontal or with a predetermined decline towards the urea plant for connecting the washing section and the urea plant, and wherein the at least one carbamate solution is fed into the pipeline within a distance of at least 3 m after said bending point of the pipeline.

14. The method according to claim 1, wherein the pipeline continues at first vertically from said expansion valve or pressure valve of the vertical washing section for a predetermined distance to a point where the pipeline is bent by a predetermined angle and continues subsequently horizontal or with a predetermined decline towards the urea plant for connecting the washing section and the urea plant, and wherein the at least one carbamate solution is fed into the pipeline within a distance of at least 1 m after said bending point of the pipeline.

15. The method according to claim 6, wherein the carbamate solution is fed into the pipeline connecting the washing section to the urea plant at up to four locations along the pipeline.

* * * * *